United States Patent [19]

Branemark

[11] Patent Number: 4,767,328
[45] Date of Patent: Aug. 30, 1988

[54] DEVICE FOR SECURING A PLURALITY OF TEETH

[75] Inventor: Per-Ingvar Branemark, Ändergatan, Sweden

[73] Assignee: The Institute for Applied Biotechnology, Gothenburg, Sweden

[21] Appl. No.: 887,498

[22] Filed: Jul. 21, 1986

[30] Foreign Application Priority Data

Jul. 24, 1985 [SE] Sweden .................... 8503580

[51] Int. Cl.⁴ .................................. A61C 13/02
[52] U.S. Cl. .............................. 433/168.1; 433/173
[58] Field of Search ............. 433/177, 176, 168, 173, 433/174, 175

[56] References Cited

U.S. PATENT DOCUMENTS

| | | | |
|---|---|---|---|
| 1,140,537 | 5/1915 | Skinner | 433/180 |
| 2,836,890 | 6/1958 | Silvis | 433/173 |
| 3,514,858 | 6/1970 | Silverman | 433/174 |
| 3,921,293 | 11/1975 | Keumurdji | 433/168.1 |
| 4,209,904 | 7/1980 | Staubli | 433/177 |
| 4,225,668 | 9/1980 | Bartoli | 433/176 |
| 4,302,189 | 11/1981 | Gillings | 433/189 |
| 4,318,696 | 3/1982 | Kasama et al. | 433/173 |
| 4,416,629 | 11/1983 | Mozsary et al. | 433/174 |

Primary Examiner—Robert Peshock
Attorney, Agent, or Firm—Armstrong, Nikaido, Marmelstein & Kubovcik

[57] ABSTRACT

The present invention relates to a device for securing a plurality of teeth to at least two attachment elements (2) implanted in the alveolar bone (1), said device comprising an essentially rigid splint (3), preferably of titanium or titanium alloy, and assembly means (5) for removably fastening a row of teeth (6) to said splint (3), the splint being arranged at least between said attachment elements (2) to absorb and distribute the load arising upon use.

7 Claims, 1 Drawing Sheet

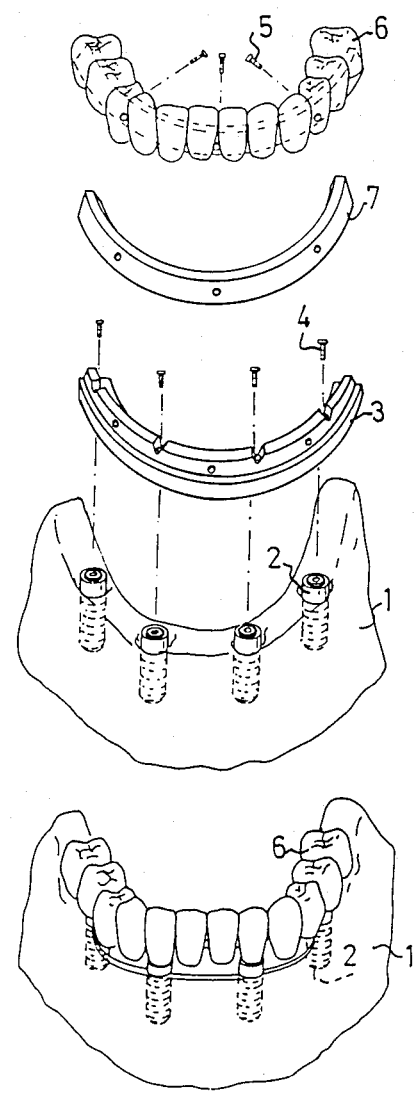

DEVICE FOR SECURING A PLURALITY OF TEETH

The present invention relates to a device for securing a plurality of teeth to a plurality of attachment elements implanted in the alveolar bone.

Within the field of odontological prosthetics a method has long been sought to enable permanent anchoring of prostheses. This is primarily because in many cases of partial or total loss of teeth, there is some difficulty in achieving satisfactory prosthesis retention using conventional methods. This is particularly so if psychological or professional factors complicate or prevent the use of removable prostheses.

Fixed prostheses are therefore required as well as conventional removable prostheses. This is also evident from the numerous methods which have been tried all over the world for permanently securing dental prostheses. Special types of implants have been used and these can be divided into two main groups. The first group constitutes implants in the form of more or less finely meshed net or a metal skeleton which is applied on the alveolar bone, either in one piece or in separate sections. In the second group the implants comprise various types of screws or pins which are anchored in the alveolar bone. Combinations of these two main groups also exist and the material used for the implants is normally stainless steel, chromium, cobalt, molybdenum alloys, etc.

However, the known implants do not function satisfactorily, many of them working loose after a short time and also causing inflammation.

A method has, however been developed for permanently anchoring individual teeth in the alveolar bone. Briefly, this method entails implanting a screw, made of titanium or titanium alloy, in a hole drilled in the bone so that the head of the screw is level with or just below the surface of the alveolar bone. The screw is then covered with a piece of mucous membrane and then left to rest for a certain period (3-6 months) to allow the bone to grow around and form a firmly bounded unit with the implanted screw. After the rest period the screw is exposed and a spacer arranged thereon, after which a single tooth prosthesis is anchored to the spacer.

A plurality of teeth can also be attached if at least two of the original teeth remain. These teeth are then cut and a hole drilled on the root side to enable a root pillar of gold to be cemented in. A bridge or "skeleton" of gold is then welded together between the teeth.

This conventional method has also been used for implants, a wax model being prepared first and then embedded in a mould, after which the wax is melted and replaced by a gold alloy. However, this method is time-consuming and expensive, as well as it being difficult to achieve the necessary precision with respect to the anchoring means. The anchoring means have therefore been unevenly loaded causing them to work loose after some time in use.

The object of the present invention is to eliminate the above-mentioned drawbacks of the known methods of securing a plurality of teeth, and to produce a device of the type described in the introduction which effects this attachment in a reliable and simple manner at relatively low cost.

This is achieved by the device according to the present invention substantially in that said device comprises an essentially rigid splint, preferably of titanium or titanium alloy, and assembly means for removably fastening a row of teeth to said splint, the splint being arranged at least between said attachment elements to absorb and distribute the load arising upon use.

The splint is prefabricated, preferably to carry a full row of teeth, the splint having suitable profile for attachment of said row of teeth, and being shaped to fit the jaw.

To further limit the load arising on the attachment elements, a resilient member may be arranged in the force-transmitting path between the row of teeth and the attachment elements.

The invention will be described in more detail in the following, with reference to the accompanying drawing showing an exploded perspective view of a preferred embodiment of a device according to the invention.

The drawing shows a device for securing a plurality of teeth to at least two attachment elements 2 implanted in the alveolar bone 1. In this case four attachment elements 2 are shown having internal screw-threads. The means also includes a splint 3 which is removably screwed to the attachment elements 2 by means of screws 4 or is fixed thereto by glueing, welding or the like, and assembly means 5 in the form of screws or the like which are used to removably fasten a row of teeth 6 to the splint 3. A resilient member 7 may be arranged in the force-transmitting path between the row of teeth 6 and the attachment elements 2.

The device proposed is preferably made of titanium or titanium alloy, as are also the attachment elements 2. The splint 3 is prefabricated and is in the form of an essentially rigid bar, preferably designed to hold a complete row of teeth 6. The splint has suitable profile for attachment of the row of teeth 6, such as L-shaped, U-shaped or the like, and is shaped to fit the jaw or alveolar bone 1. The splint 3 is thus arranged at least between the attachment elements 2, but preferably extending the entire length of the jaw. This enables attachment elements 2 to be placed at the most suitable places for implantation. The rigidity of the splint 3 ensures that the load arising upon use will be absorbed and distributed, thus reducing the risk of the attachment elements 2 working loose from the alveolar bone. This risk can be further reduced by inserting a resilient member 7, consisting of acryllic plastic, silicon, rubber or the like, in the force-transmitting path between the row of teeth 6 and the attachment elements 2. The resilient member 7 may consist of a resilient strip or layer arranged between the row of teeth and the splint, or of a resilient ring arranged between each attachment element 2 and the splint 3.

The present invention thus enables permanent anchoring of a dental prosthesis which, however, can easily be removed if required. The prefabricated splint saves both time and expense in the preparation and fitting of the prosthesis, while its rigid construction reduces the load on the individual attachment elements.

The invention is not limited to the embodiment shown in the drawing. It can be modified in many ways within the scope of the following claims.

I claim:

1. A device for securing a plurality of teeth to the alveolar bone, comprising, a plurality of implant attachment elements capable of being attached to the alveolar bone, an essentially rigid splint having an arc shape to fit the curve of the alveolar bone and being attachable to said plurality of implant attachment elements, a plurality of attached false teeth, an assembly means for removably attaching said plurality of attached false teeth to said splint, wherein said rigid splint functions as a force distribution means during use.

2. The device according to claim 1, wherein a resilient member is positioned between said false teeth and said rigid splint.

3. The device according to claim 2, wherein said resilient member is resilient strip or layer positioned between said plurality of false teeth and said splint.

4. The device according to claim 2, wherein said resilient member comprises a plurality of resilient rings, one of which is positioned between each of said plurality of implant attachment elements and said splint.

5. The device according to claim 1, wherein said assembly means comprises a plurality of screws capable of screwing said plurality of teeth to said splint.

6. The device according to claim 1, wherein said splint is removably attached to said implant attachment elements by a plurality of screws.

7. The device according to claim 1, wherein said splint is glued or welded to said plurality of attachment elements.

* * * * *